(12) United States Patent
Fortin

(10) Patent No.: US 12,226,390 B2
(45) Date of Patent: *Feb. 18, 2025

(54) CANNABINOIDS COMPOSITIONS WITH POLYUNSATURATED FATTY ACID MONOGLYCERIDES, METHODS AND USES THEREOF

(71) Applicant: SCF PHARMA INC., Sainte-Luce (CA)

(72) Inventor: Samuel C. Fortin, Sainte-Luce (CA)

(73) Assignee: SCF PHARMA INC., Sainte-Luce (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/199,797

(22) Filed: May 19, 2023

(65) Prior Publication Data
US 2023/0355564 A1 Nov. 9, 2023

Related U.S. Application Data

(63) Continuation of application No. 17/269,253, filed as application No. PCT/CA2020/051007 on Jul. 21, 2020, now abandoned, which is a continuation-in-part of application No. 16/517,607, filed on Jul. 21, 2019, now Pat. No. 10,716,776, and a continuation-in-part of application No. 16/910,055, filed on Jun. 23, 2020, now Pat. No. 11,478,443, which is a continuation of application No. 16/517,607, filed on Jul. 21, 2019, now Pat. No. 10,716,776.

(60) Provisional application No. 62/886,400, filed on Aug. 14, 2019.

(51) Int. Cl.
| | |
|---|---|
| *A61K 31/232* | (2006.01) |
| *A61K 31/05* | (2006.01) |
| *A61K 31/192* | (2006.01) |
| *A61K 31/352* | (2006.01) |
| *A61K 35/60* | (2006.01) |
| *A61K 36/185* | (2006.01) |

(52) U.S. Cl.
CPC ............ *A61K 31/232* (2013.01); *A61K 31/05* (2013.01); *A61K 31/192* (2013.01); *A61K 31/352* (2013.01); *A61K 35/60* (2013.01); *A61K 36/185* (2013.01)

(58) Field of Classification Search
None
See application file for complete search history.

(56) References Cited

U.S. PATENT DOCUMENTS

| | | |
|---|---|---|
| 6,180,671 B1 | 1/2001 | Freedman et al. |
| 6,552,081 B1 | 4/2003 | Freedman et al. |
| 7,138,431 B1 | 11/2006 | Chilton |
| 7,981,915 B2 | 7/2011 | Freedman |
| 8,119,690 B2 | 2/2012 | Fortin |
| 8,198,324 B2 | 6/2012 | Fortin |
| 8,222,295 B2 | 7/2012 | Fortin |
| 8,329,747 B2 | 12/2012 | Fortin |
| 8,722,737 B2 | 5/2014 | Fortin |
| 8,816,110 B2 | 8/2014 | Fortin |
| 9,101,563 B2 | 8/2015 | Fortin |
| 9,233,915 B2 | 1/2016 | Fortin |
| 9,447,020 B2 | 9/2016 | Fortin |
| 9,480,660 B2 | 11/2016 | Fortin |

(Continued)

FOREIGN PATENT DOCUMENTS

| | | |
|---|---|---|
| CA | 2538382 | 3/2005 |
| CA | 2599473 | 9/2006 |

(Continued)

OTHER PUBLICATIONS

Herbst et al., "Omega-3 supplementation alters mitochondrial membrane composition and respiration kinetics in human skeletal muscle", J. Physiol. 592.6 (Jan. 6, 2014) pp. 1341-1352.

(Continued)

*Primary Examiner* — Michael V Meller
(74) *Attorney, Agent, or Firm* — Smart & Biggar LP

(57) ABSTRACT

There are provided compositions comprising at least one compound chosen from compound of formula (I), compound of formula (II), compound of formula (III) and compound of formula (IV):

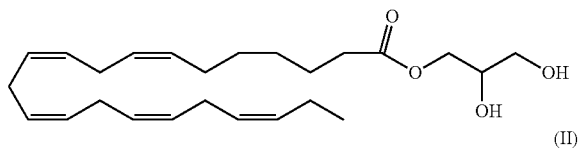

(I)

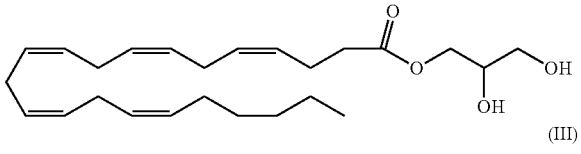

(II)

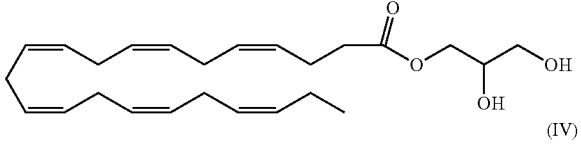

(III)

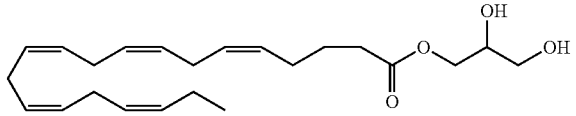

(IV)

and a cannabinoid extract.

12 Claims, 3 Drawing Sheets

(56) References Cited

U.S. PATENT DOCUMENTS

| | | | |
|---|---|---|---|
| 9,670,133 | B2 | 6/2017 | Koch et al. |
| 9,925,165 | B2 | 3/2018 | Fortin |
| 10,716,776 | B2 | 7/2020 | Fortin |
| 2002/0188024 | A1 | 12/2002 | Chilton et al. |
| 2004/0214799 | A1 | 10/2004 | Mukai et al. |
| 2006/0121583 | A1 | 6/2006 | Lassalle et al. |
| 2009/0291102 | A1 | 11/2009 | Fortin |
| 2009/0292019 | A1 | 11/2009 | Fortin |
| 2010/0160261 | A1 | 6/2010 | Fortin |
| 2010/0196496 | A1 | 8/2010 | Fortin |
| 2012/0213872 | A1 | 8/2012 | Fortin |
| 2012/0251582 | A1 | 10/2012 | Fortin |
| 2013/0059911 | A1 | 3/2013 | Fortin |
| 2015/0119591 | A1 | 4/2015 | Fortin |
| 2015/0343071 | A1 | 12/2015 | Vangara et al. |
| 2017/0049830 | A1 | 2/2017 | Raderman |
| 2018/0078504 | A1 | 3/2018 | Sacks et al. |
| 2018/0264121 | A1 | 9/2018 | Donaduzzi et al. |
| 2019/0133992 | A1 | 5/2019 | Shaaban |
| 2019/0231833 | A1 | 8/2019 | Garti et al. |
| 2019/0314326 | A1 | 10/2019 | Garti et al. |
| 2019/0374502 | A1 | 12/2019 | Jha |
| 2020/0121606 | A1 | 4/2020 | Sacks et al. |
| 2020/0316007 | A1 | 10/2020 | Fortin |

FOREIGN PATENT DOCUMENTS

| | | |
|---|---|---|
| EP | 1352648 | 10/2003 |
| EP | 1 962 825 B1 | 4/2014 |
| JP | 2010132631 | 6/2010 |
| WO | 2002064166 | 8/2002 |
| WO | 2002089787 | 11/2002 |
| WO | 2002096408 | 12/2002 |
| WO | 2004000333 | 12/2003 |
| WO | 2004024136 | 3/2004 |
| WO | 2004064716 | 8/2004 |
| WO | 2006117668 | 11/2006 |
| WO | 2008036353 | 3/2008 |
| WO | 2008113177 | 9/2008 |
| WO | 2011/092299 A1 | 8/2011 |
| WO | 2015063041 | 5/2015 |
| WO | 2016066460 | 5/2016 |
| WO | 2017216362 | 12/2017 |
| WO | 2018061007 A1 | 4/2018 |
| WO | 2018204326 | 11/2018 |
| WO | 2019210424 A1 | 7/2019 |
| WO | 2019153073 | 8/2019 |
| WO | 2019234728 | 12/2019 |
| WO | 2020028991 | 2/2020 |
| WO | 2020044118 | 3/2020 |
| WO | 2021012046 A1 | 1/2021 |
| WO | 2021022378 | 2/2021 |

OTHER PUBLICATIONS

Johnson et al., "Eicosapentaenoic acid but not docosahexaenoic acid restores skeletal muscle mitochondrial oxidative capacity in old mide", Aging Cell (2015) 14, pp. 734-743.

Morin et al., "Docosapentaenoic acid monoacylglyceride reduces inflammation and vascular remodeling in experimental pulmonary hypertension", Am J Physiol Heart Circ Physiol 307: H574-H586, Jun. 14, 2014.

Swanson et al., "Omega-3 Fatty Acids EPA and DHA: Health Benefits Throughout Life", American Society for Nutrition. Adv. Nutr. 3: 1-7, 2012.

Egil Fosslien, "Review: Mitochondrial Meidine—Molecular Pathology of Defective Oxidative Phosphorylation", Annals of Clinical & Laboratory Science, vol. 31, No. 1, 2001, pp. 25-67.

Marsicano et al., "Neuroprotective properties of cannabinoids against oxidative stress: role of the cannabinoid receptor CB1", Journal of Neurochemistry, vol. 80, Issue 3, Jan. 21, 2002.

Abstract of Herrera et al., "The CB2 cannabinoid receptor signals apoptosis via ceramide-dependent activation of the mitochondrial intrinsic pathway", Experimental Cell Research, vol. 312, Issue 11, Jul. 1, 2006, pp. 2121-2131.

Abstract of Athanasiou et al., "Cannabinoid receptor agonists are mitochondrial inhibitors: A unified hypothesis of how cannabinoids modulate mitochondrial function and induce cell death", Biomedical and Biophysical Research Communications, vol. 364, Issue 1, Dec. 7, 2007, pp. 131-137.

Tedesco et al., "Cannabinoid Type 1 Receptor Blockade Promotes Mitochondrial Biogenesis Through Endothelial Nitric Oxide Synthase Expression in White Adipocytes", Diabetes, vol. 57, Aug. 2008.

Turmeric—The Genus *Curcuma*, Edited by P.N. Ravindran et al., Jul. 24, 2006.

Akoh, "Lipase-Catalyzed Synthesis or Partial Glyceride", Biotechnology Letters, vol. 15, No. 9 (Sep. 1993) pp. 949-954.

Ando et al., "Reinvestigation of Positional Distribution of Fatty Acids in Docosahexaenoic Acid-Rich Fish Oil Triacyl-sn-glycerols", Lipids, vol. 35, No. 5 (2000) pp. 579-582.

Beharry et al., "Long-term docosahexaenoic acid therapy in a congenic murine model of cystic fibrosis", Am J Physiol Gastrointest Liver Physiol 292:G839-G848, 2007. First Published Nov. 9, 2006.

Chau et al., "Monoglyceride and diglyceride lipases from human platelet microsomes", Biochimica et Biophysica Acta, 963 (Jun. 1988) 436-444.

Duvoix et al., "Chemopreventive and therapeutic effects of curcumin", Cancer Letters 223 (2005) 181-190.

English Abstract of JP02131418, "Comparison of enhanced and routine methods for measuring ambient low-level sulfur dioxide", published on May 21, 1990.

English Abstract of JP7149786, "Glyceroglycolipid and Carcinogenic Promoter Inhibitor" published on Jun. 13, 1995.

English Abstract of JP62077319, "Anticancer pharmaceuticals containing eicosapentaenoic acid, its esters, or glycerides", published on Apr. 9, 1987.

English Abstract of JP2000044588, "Novel monoacylglycosyl monoacylglycerols for surfactants", published on Feb. 15, 2000.

Li et al., "Biosynthesis of Docosahexaenoate-Containing Glycrolipid Molecular Species in the Retina", Journal of Molecular Neuroscience, vol. 16, Nov. 1, 2001.

Freedman et al., "Fatty acids in cystic fibrosis", Current Opinion in Pulmonary Medicine 2000, 6:530-532.

Kafrawy et al., "Docosahexaenoic acid in phosphatidylcholine mediates cytotoxicity more effectively than other ω-3 and ω-6 fatty acids", Cancer Letters 132 (May 19, 1998) 23-29.

Kawashima et al., "Inhibition of Rat Liver Microsomal Desaturases by Curcumin and Related Compounds", Biosci. Biotech Biochem 60 (1), 108-110, 1996.

Kawashima et al., "Nicardipine and Nifedipine Inhibit Fatty Acid Desaturases in Rat Liver Microsomes", Biosci. Biotech. Biochem., 60 (10), 1672-1676, 1996.

Kawashima et al., "Inhibotory effects of alkyl and its derivatives on fatty acid desaturation", Biochimica et Biophysica Acta 1299 (1996) 34-38.

Kawashima et al., "Enzymatic Synthesis of High-Purity Structured Lipids with Caprylic Acid at 1,3-Positions and Polyunsaturated Fatty Acid at 2-Position", JAOCS, vol. 78, No. 6 (2001).

Martin et al., "The safety and efficacy of oral docosahexaenoic acid supplementation for the treatment of primary sclerosing cholangitis—a pilot study", Aliment Pharmacol Ther 2012; 35: 255-265.

Monks et al., "Feasibility of a High-Flux Anticancer Drug Screen Using a Diverse Panel of Cultured Human Tumor Cell Lines", Articles, vol. 83, No. 11, Jun. 5, 1991.

Abstract of Myrdal et al., "Solubilization of Drugs in Aqueous Media", Encyclopedia of Pharmaceutical Technology, published on Oct. 2, 2006.

Nakano et al., "Inhibitory Effects of Capsaicinoids on Fatty Acid Desaturation in a Rat Liver Cell Line", Biosci. Biotechnol. Biochem., 65 (8), 1859-1863, Mar. 29, 2001.

Ohta et al., Action of a New Mammalian DNA Polymerase Inhibitor, Sulfoquinovosyldiacylglycerol, Biol. Pharm. Bull. 22 (2) 111-116, Feb. 1999.

(56) References Cited

OTHER PUBLICATIONS

Pacetti et al., "High performance liquid chormatography-tandem mass spectometry of phospholipid molecular species in eggs from hen fed diets enriched in seal blubber oil", Journal of Chromatography A, 1097 (Aug. 30, 2005) 66-73.

Abstract of Rohan et al., "Dietary factors and survival from breast cancer", Nutr Cancer, 1993;20(2):167-177.

Rose et al., "Omega-3 fatty acids as cancer chemopreventive agents", Pharmacology & Therapeutics 83 (1999) 217-244.

Rosu et al., "Enzymatic synthesis of glycerides from DHA-enriched PUFA ethyl ester by glycerolysis under vacuum", Journal of Molecular Catalysis B: Enzymatic 4 (1998) 191-198.

Rubinstein et al., "Comparison of In Vitro Anticancer-Drug-Screening Data Generated With a Tetrazolium Assay Versus a Protein Assay Against a Diverse Panel of Human Tumor Cell Lines", Articles, vol. 82, No. 13, Jul. 4, 1990.

Schaaf et al., "Polyunsaturated Monoglycerides and a Pregnadiene in Defensive Glands of the Water Beetle *Agabus affinis*", Lipids, vol. 35, No. 5 (2000).

Shimizu et al., "Sesamin is a Potent and Specific Inhibitor of A5 Desaturase in Polyunsaturated Fatty Acid Biosynthesis", Lipids, vol. 26, No. 7 (1991).

Skehan et al., "New Colorimetric Cytotoxicity Assay for Anticancer-Drug Screening", Articles, vol. 82, No. 13, Jul. 4, 1990.

Tanaka et al., "Preparative Separation of Acylglycerol by Centrifugal Partition Chromatography (CPC)", Thermochimica (1992).

Vandevoorde et al., "Influence of the degree of unsaturation of the acyl side chain upon the interaction of analogues of 1-arachdonoylglycerol with monoacylglycerol lipase and fatty acid amid hydrolase", Biochemical and Biophysical Research Communication 337 (Sep. 13, 2005) 104-109.

Watanabe et al., "Chemical signals involved in larval metamorphosis in Hydroides ezoensis (Serpulidae; Polychaeta). Part II: Isolation and identification of a new monoacyl glycerol from adult tube clumps as a metamorphosis-inducing substance", J Mar Biotechnol (1998) 6:11-15.

Watanabe et al., "n-3 Polyunsaturated fatty acid (PUFA) deficiency elevates and n-3 PUFA enrichment reduces brain 2-arachidonoylglycerol level in mice", Prostaglandins, Leukotrienes and Essential Fatty Acids 69 (Mar. 20, 2003) 51-59.

Yamane et al., "Multiple Intensified Performance of an Enzyme-Catalyzed Reaction in Organic Medium", Analysis New York Academy Sciences (1988).

Zerouga et al., "Synthesis of a novel phosphatidylcholine conjugated to docosahexaenoic acid and methotrexate that inhibits cell proliferation", Anti-Cancer Drugs 2002, pp. 301-311.

Debora Cutuli, "Functional and Structural Benefits Induced by Omega-3 Polyunsaturated Fatty Acids During Agin", Current Neuropharmacology, 2017, 15, 534-542.

English Abstract of JP2010132631A, "Composition Having Inverse Agonist and Antagonist Activities of Cannabicoid Receptor", published on Jun. 17, 2010.

Flachs et al., "Polyunsaturated fatty acids of marine origin upregulate mitochondrial biogenesis and induce β-oxidation in white fat", Diabetologia (Oct. 5, 2005) 48: 2365-2375.

Cockbain et al., "Omega-3 polyunsaturated fatty acids for the treatment and prevention of colorectal cancer", Gut 2012; 61: 135-149 (Published Online First: Apr. 13, 2011).

Barry et al., "Anticancer Agents. IV. 1a,b The antitumor Activity of Some 1,4- and 1,5-(Bisthiosemicarbazones) and of Related Heterocycles" Journal of Meidcinal Chemistry, 1970, vol. 13, No. 3.

Liang et al., "Effect of dietary omega-3 fatty acids on tumor-associated macrophages and prostate cancer progression", Prostate, Oct. 2016, 76(14): 1293-1302.

Newell et al., "A Critical Review on the Effect of Docosahexaenoic Acid (DHA) on Cancer Cell Cycle Progression", Int J Mol Sci. Aug. 2017; 18(8): 1784.

Ramsaywack et al., "Synthesis and Surface Investigations of N-Substitued 2,5-Dithio-7-azabicyclo[2.2.1]heptanes on Gold Surfaces", J. Phys. Chem. C Mar. 16, 2012, 116, 7886-7896.

Shao et al., "Structural characterization of self-assemblies of new omega-3 lipids: docosahexaenoic acid and docosapentaenoic acid monoglycerides", Phys. Chem. Phys., Aug. 31, 2018, 20, 23928.

Vairoletti et al., "Synthesis of bicyclic 1,4-thiazepines as novel anti-Trypanosoma brucei brucei agents", Med. Chem. Commun., Jun. 11, 2019, 10, 1481.

Zgair et al., "Oral administration of cannabis with lipids leads to high levels of cannabinoids in the intestinal lymphatic system and prominent immunomodulation", Scientific Reports, 7:14542, Published online: Nov. 6, 2017.

Zhdanko et al., "One-step synthesis of N-acetylcysteine and glutathione derivatives using the Ugi reaction", Tetrahedron 65 (Apr. 17, 2009) 4692-4702.

Zgair et al., "Dietary fats and pharmaceutical lipid excipients increase systemic exposure to orally administered cannabis and cannabis-based medicines", Am J Transl Res 2016;8(8):3448-3459; published on Aug. 30, 2016.

Davani-Davari et al., "Prebiotics: Definition, Types, Sources, Mechanisms, and Clinical Application", Foods 2019, 8, 92 (Published Mar. 9, 2019).

Gibson et al., "Dietary Modulation of the Human Colonic Microbiota: Introducing the Concept of Prebiotics", MRC Dunn Clinical Nutrition Centre, Cambridge, UK and Unité de Biochimie Toxicologique et Cancérologue, Départ. des Sci. Pharmaceutiques, Université Catholique de Louvain, Brussels, Belgium, American Institute of Nutrition 1995. (The year of publication is sufficiently earlier than the effective U.S. filing date so that the particular month of publication is not an issue).

Png et al., "Mucolytic Bacteria With Increased Prevalence in IBD Mucosa Augment In Vitro utilization of Mucin by Other Bacteria", Am J. Gastroenterol 2020; 105:2420-2428 (published online Jul. 20, 2010).

Alcock et al., "Fatty acids from diet and microbiota regulate energy metabolism" [version 1; referees: 2 approved], F1000 Research 2015, F(F1000 Faculty Rev): 738 / Last updated: Sep. 10, 2015.

Constantini et al., "Impact of Omega-3 Fatty Acids on the Gut Microbiota", Int. J. Mol. Sci. Dec. 7, 2017, 18, 2645.

Khaddaj-Mallat et al., "Novel n-3 PUFA monoacylglycerides of pharmacological and medicinal interest: Anti-inflammatory and anti-proliferative effects", European Journal of Pharmacology 792 (Oct. 31, 2016) 70-77.

Piazzi et al., "Eicosapentaenoic acid free fatty acid prevents and suppresses colonic neoplasia in colitis-associated colorectal cancer acting on Notch signaling and gut microbiota", Int. J. Cancer: 135, 2004-2013 (Mar. 19, 2014).

Derrien et al., "Akkermansia muciniphila and its role in regulating host functions", Microbial Pathogenesis 106 (2017) 171-1/1. (The year of publication is sufficiently earlier than the effective U.S. filing date so that the particular month of publication is not an issue).

Cani et al., "Next-Generation Beneficial Microbes: The Case of Akkermansia muciniphila", Frontiers in Microbiology, Sep. 2017, vol. 8, Article 1765.

Jocelyn Kaiser, "Gut microbes shape response to cancer immunotherapy", Science, Nov. 3, 2017, vol. 358, Issue 6363.

Gomes et al., "*Bifidobacterium* spp. and Lactobacillus acidophilus: biological, biochemical, technological and therapeutical properties relevant for use as probiotics", Trends in Food Science & Technology 10 (1999) 139-157. (The year of publication is sufficiently earlier than the effective U.S. filing date so that the particular month of publication is not an issue).

Arora et al., "The gut microbiota and metabolic disease: current understanding and future perspectives", Journal of Internal Medicine, 2016, 280; 339-349. (The year of publication is sufficiently earlier than the effective U.S. filing date so that the particular month of publication is not an issue).

Scott et al., "Manipulating the gut microbiota to maintain health and treat disease", Microbial Ecology in Health and Disease (Feb. 2, 2015), 26: 25877.

Csekes, E. et al., "Skin Aging Cellular Senescence and Natural Polyphenols". Int. J. Mol. Sci., Nov. 23, 2021 (Nov. 23, 2021), vol. 22(23), p. 12641.

(56) References Cited

OTHER PUBLICATIONS

Cuenoud, B., et al., "Monoacylglycerol Form of Omega-3s Improves Its Bioavailability in Humans Compared to Other Forms". Nutrients, Jul. 4, 2020 (Jul. 4, 2020), vol. 12, p. 1014.
Champigny, C.M., et al., "Omega-3 Monoacylglyceride Effects on Longevity, Mitochondrial Metabolism and Oxidative Stress: Insights from *Drosophila melanogaster*". Mar. Drugs, Nov. 16, 2018 (Nov. 16, 2018), vol. 16, pp. 453-468.
Bhatt et al., "Cardiovascular Risk Reduction with Icosapent Ethyl for Hypertriglyceridemia". The New England Journal of Medicine, vol. 380, No. 1 (Jan. 2019).
Meek et al., "Non-Steroidal Anti-Inflammatory Drugs: An Overview of Cardiovascular Risks". Pharmaceuticals, 2010, 3, 2146-2162.
Sun et al., "Withdrawal of COX-2 selective inhibitors rofecoxib and valdecoxib: impact on NSAID and gastroprotective drug prescribing and utilization". Current Medical Research and Opinions, vol. 23, No. 8, 2007, 1859-1866.
Brideau et al., "A human whole blood assay for clinical evaluation of biochemical efficacy of cyclooxygenase inhibitors". Inflamm Res 45:68-74 (1996).

CANNABINOIDS COMPOSITIONS WITH POLYUNSATURATED FATTY ACID MONOGLYCERIDES, METHODS AND USES THEREOF

CROSS-REFERENCE TO RELATED APPLICATIONS

The present application is a continuation of U.S. Ser. No. 17/269,253 filed on Feb. 18, 2021, that is a 35 USC 371 national stage entry of PCT/CA2020/051007 filed on Jul. 21, 2020, that is a continuation-in-part of U.S. Ser. No. 16/517,607 filed on Jul. 21, 2019 (issued as U.S. Pat. No. 10,716,776 on Jul. 21, 2020) and of U.S. Ser. No. 16/910,055 filed on Jun. 23, 2020 (issued as U.S. Pat. No. 11,478,443 on Oct. 25, 2022) that is a continuation of Ser. No. 16/517,607 filed on Jul. 21, 2019 (issued as U.S. Pat. No. 10,716,776 on Jul. 21, 2020). PCT/CA2020/051007 also claims priority to U.S. 62/886,400 filed on Aug. 14, 2019. These documents are hereby incorporated by reference in their entirety.

FIELD OF THE DISCLOSURE

The present document relates to the field of organic chemistry. More particularly, it relates to polyunsaturated fatty acid monoglyceride combinations with cannabinoids thereof. It also provides methods for treating inflammatory disease without the psychotropic effect of some cannabinoids.

BACKGROUND OF THE DISCLOSURE

Traditionally, cannabis was consumed by smoking the dry flowers or the resin of the plant. With the recent evidence of health benefit of some cannabinoids found in the flowers or resin, like cannabidiol (CBD) or cannabidiolic acid (CBDA), per os formulations was developed. Lipids formulation of cannabinoids gains in popularity since Zgair shows that oral co-administration of cannabinoids with lipids can substantially increase their intestinal lymphatic transport (Zgair, A., et al., *Oral administration of cannabis with lipids leads to high levels of cannabinoids in the intestinal lymphatic system and prominent immunomodulation*. Scientific Reports, 2017. 7(1): p. 14542).

SUMMARY OF THE DISCLOSURE

There is provided a composition comprising at least one compound chosen from compound of formula (I), compound of formula (II), compound of formula (III) and compound of formula (IV):

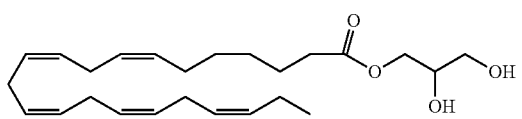

(I)

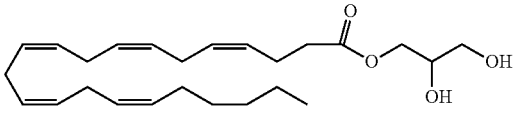

(II)

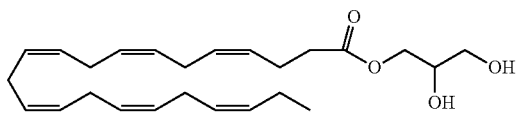

(III)

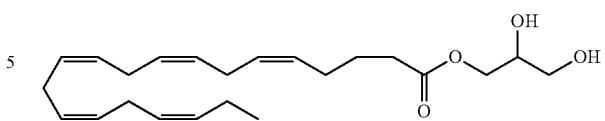

(IV)

and a cannabinoid extract.

There is also provided a composition comprising at least one synthetic SN1 monoglyceride of fish oil and at least one isolated cannabinoid.

There is also provided a composition comprising at least one synthetic SN1 monoglyceride of fish oil; a synthetic diglyceride of fish oil selected from the group consisting of SN 1,2 synthetic diglyceride and SN 1,3 synthetic diglyceride; and at least one isolated cannabinoid.

There is also provided a composition comprising at least one synthetic SN1 monoglyceride of a vegetal or animal oil and at least one isolated cannabinoid.

There is also provided a composition comprising at least one synthetic SN1 monoglyceride of a vegetal or animal oil; a synthetic diglyceride of vegetal or animal oil selected from the group consisting of SN 1,2 synthetic diglyceride and SN 1,3 synthetic diglyceride; and at least one isolated cannabinoid.

There is also provided a composition comprising at least one compound chosen from compound of formula (I), compound of formula (II), compound of formula (III) and compound of formula (IV) and at least one cannabinoid chosen from Tetrahydrocannabinol (THC), Tetrahydrocannabinolic acid (THCA), Cannabidiol (CBD), Cannabidiolic Acid (CBDA) and mixtures thereof.

There is also provided a composition comprising at least one compound chosen from compound of formula (I), compound of formula (II), compound of formula (III) and compound of formula (IV) and Tetrahydrocannabinolic acid (THCA).

There is also provided a composition comprising at least one compound chosen from compound of formula (I), compound of formula (II), compound of formula (III) and compound of formula (IV) and Cannabidiol (CBD).

There is also provided a composition comprising at least one compound chosen from compound of formula (I), compound of formula (II), compound of formula (III) and compound of formula (IV) and Cannabidiolic Acid (CBDA).

There is also provided a composition comprising at least one compound chosen from compound of formula (I), compound of formula (II), compound of formula (III) and compound of formula (IV) and Tetrahydrocannabinol (THC).

There is also provided a composition comprising:
  at least one compound chosen from compound of formula (I), compound of formula (II), compound of formula (III) and compound of formula (IV);
  cannabidiol (CBD) in a concentration of at least 0.1% by weight, based on the total weight of the composition; and
  tetrahydrocannabinol (THC) in a concentration of less than 0.3% by weight, based on the total weight of the composition.

There is also provided a composition comprising:
  at least one compound chosen from compound of formula (I), compound of formula (II), compound of formula (III) and compound of formula (IV);

cannabidiolic acid (CBDA) in a concentration of at least 0.1% by weight, based on the total weight of the composition; and
tetrahydrocannabinol (THC) in a concentration of less than 0.3% by weight, based on the total weight of the composition.
There is also provided a composition comprising:
at least one compound chosen from compound of formula (I), compound of formula (II), compound of formula (III) and compound of formula (IV);
tetrahydrocannabinol (THC) in a concentration of at least 0.1 by weight, based on the total weight of the composition; and
cannabidiol (CBD) in a concentration of at least 0.1% by weight, based on the total weight of the composition.
There is also provided a composition comprising:
at least one compound chosen from compound of formula (I), compound of formula (II), compound of formula (III) and compound of formula (IV);
cannabidiolic acid (CBDA) in a concentration about 0.1% to about 50% by weight, based on the total weight of the composition; and
tetrahydrocannabinolic acid (THCA) in a concentration less than 0.3% by weight, based on the total weight of the composition.
There is also provided a composition comprising:
at least one compound chosen from compound of formula (I), compound of formula (II), compound of formula (III) and compound of formula (IV);
at least one cannabinoid; and
at least one lipid.
There is also provided a composition comprising:
about 10% to about 25% by weight, based on the total weight of the composition, of at least one compound chosen from compound of formula (I), compound of formula (II), compound of formula (III) and compound of formula (IV);
about 0.1% to about 30% by weight, based on the total weight of the composition, of at least one cannabinoid; and
about 30% to about 60% by weight, based on the total weight of the composition, of at least one lipid.
There is also provided a composition comprising:
about 10% to about 25% by weight, based on the total weight of the composition, of at least one compound chosen from compound of formula (I), compound of formula (II), compound of formula (III) and compound of formula (IV);
about 0.1% to about 10% by weight, based on the total weight of the composition, of at least one cannabinoid extract; and
about 30% to about 60% by weight, based on the total weight of the composition, of at least one lipid.
There is also provided a composition comprising:
at least one compound chosen from compound of formula (I), compound of formula (II), compound of formula (III) and compound of formula (IV);
a cannabinoid extract; and
at least one lipid.
There is also provided a composition comprising:
at least one compound chosen from compound of formula (I), compound of formula (II), compound of formula (III) and compound of formula (IV);
at least one cannabinoid chosen from Tetrahydrocannabinol (THC), Tetrahydrocannabinolic acid (THCA), Cannabidiol (CBD) and Cannabidiolic Acid (CBDA);
at least one lipid.
There is also provided a composition comprising:
at least one compound chosen from compound of formula (I), compound of formula (II), compound of formula (III) and compound of formula (IV);
at least one cannabinoid that is Tetrahydrocannabinolic acid (THCA); and
at least one lipid.
There is also provided a composition comprising:
at least one compound chosen from compound of formula (I), compound of formula (II), compound of formula (III) and compound of formula (IV);
at least one cannabinoid that is Cannabidiol (CBD); and
at least one a lipid.
There is also provided a composition comprising:
at least one compound chosen from compound of formula (I), compound of formula (II), compound of formula (III) and compound of formula (IV);
at least one cannabinoids that is Cannabidiolic Acid (CBDA); and
at least one lipid.
There is also provided a composition comprising:
at least one compound chosen from compound of formula (I), compound of formula (II), compound of formula (III) and compound of formula (IV);
at least one cannabinoids is Tetrahydrocannabinol (THC); and
at least one lipid.
There is also provided a composition comprising:
at least one compound chosen from compound of formula (I), compound of formula (II), compound of formula (III) and compound of formula (IV);
cannabidiol (CBD) in a concentration of at least 0.1% by weight, based on the total weight of the composition;
tetrahydrocannabinol (THC) in a concentration of less than 0.3% by weight, based on the total weight of the composition; and
at least one lipid.
There is also provided a composition comprising:
at least one compound chosen from compound of formula (I), compound of formula (II), compound of formula (III) and compound of formula (IV);
cannabidiolic acid (CBDA) in a concentration of at least 0.1% by weight, based on the total weight of the composition;
tetrahydrocannabinol (THC) in a concentration of less than 0.3% by weight, based on the total weight of the composition; and
at least one lipid.
There is also provided a composition comprising:
at least one compound chosen from compound of formula (I), compound of formula (II), compound of formula (III) and compound of formula (IV);
cannabidiolic acid (CBDA) in a concentration of at least 0.1% by weight, based on the total weight of the composition;
tetrahydrocannabinol (THC) in a concentration of at least 0.1% by weight, based on the total weight of the composition; and
at least one lipid.
There is also provided a composition comprising:
at least one compound chosen from compound of formula (I), compound of formula (II), compound of formula (III) and compound of formula (IV);
cannabidiolic acid (CBDA) in a concentration about 0.1% to about 75% by weight, based on the total weight of the composition;

tetrahydrocannabinolic acid (THCA) in a concentration less than 0.3% by weight, based on the total weight of the composition; and
at least one lipid.

There is also provided a composition comprising:
at least one compound chosen from compound of formula (I), compound of formula (II), compound of formula (III) and compound of formula (IV);
cannabidiol (CBD) in a concentration about 0.1% to about 75% by weight, based on the total weight of the composition;
tetrahydrocannabinol (THC) in a concentration less than 0.3% by weight, based on the total weight of the composition; and
at least one lipid.

There is also provided a composition comprising:
at least one compound chosen from compound of formula (I), compound of formula (II), compound of formula (III) and compound of formula (IV);
cannabidiolic acid (CBDA) in a concentration about 0.1% to about 50% by weight, based on the total weight of the composition;
tetrahydrocannabinolic acid (THCA) in a concentration less than 0.3% by weight, based on the total weight of the composition; and
at least one lipid.

There is also provided a composition comprising:
at least one compound chosen from compound of formula (I), compound of formula (II), compound of formula (III) and compound of formula (IV);
cannabidiol (CBD) in a concentration about 0.1% to about 50% by weight, based on the total weight of the composition;
tetrahydrocannabinol (THC) in a concentration less than 0.3% by weight, based on the total weight of the composition; and
at least one lipid.

There is also provided a composition comprising:
at least one compound chosen from compound of formula (I), compound of formula (II), compound of formula (III) and compound of formula (IV);
cannabidiol (CBD) in a concentration about 0.1% to about 5% by weight, based on the total weight of the composition;
tetrahydrocannabinol (THC) in a concentration about 0.1% to about 5% by weight, based on the total weight of the composition; and
at least one lipid.

There is also provided a composition comprising:
at least one compound chosen from compound of formula (I), compound of formula (II), compound of formula (III) and compound of formula (IV);
cannabidiolic acid (CBDA) in a concentration about 0.1% to about 5% by weight, based on the total weight of the composition;
tetrahydrocannabinolic acid (THCA) in a concentration less than 0.3% by weight, based on the total weight of the composition; and
at least one lipid.

There is also provided a composition comprising:
at least one compound chosen from compound of formula (I), compound of formula (II), compound of formula (III) and compound of formula (IV);
cannabidiolic acid (CBDA) in a concentration about 3% to about 10% by weight, based on the total weight of the composition;
tetrahydrocannabinolic acid (THCA) in a concentration less than 0.3% by weight, based on the total weight of the composition; and
at least one lipid.

There is also provided a method for increasing plasma cannabinoid concentration of a subject in need thereof, said method comprising administering an effective amount of:
at least one compound chosen from compound of formula (I), compound of formula (II), compound of formula (III) and compound of formula (IV); and
at least one cannabinoid.

There is also provided a method for increasing plasma cannabinoid concentration of a subject in need thereof, said method comprising administering an effective amount of:
at least one compound chosen from compound of formula (I), compound of formula (II), compound of formula (III) and compound of formula (IV);
at least one cannabinoid; and
at least one lipid.

There is also provided a method for increasing plasma cannabinoid concentration of a subject in need thereof, said method comprising administering an effective amount of:
at least one compound chosen from compound of formula (I), compound of formula (II), compound of formula (III) and compound of formula (IV); and
a cannabinoid extract.

There is also provided a method for increasing plasma cannabinoid concentration of a subject in need thereof, said method comprising administering an effective amount of:
at least one compound chosen from compound of formula (I), compound of formula (II), compound of formula (III) and compound of formula (IV)';
a cannabinoid extract; and
at least one lipid.

There is also provided a method for increasing the plasma cannabidiol (CBD) concentration of a subject in need thereof, said method comprising administering an effective amount of:
at least one compound chosen from compound of formula (I), compound of formula (II), compound of formula (III) and compound of formula (IV); and
cannabidiol (CBD).

There is also provided a method for increasing plasma tetrahydrocannabinol (THC) concentration of a subject in need thereof, said method comprising administering an effective amount of:
at least one compound chosen from compound of formula (I), compound of formula (II), compound of formula (III) and compound of formula (IV); and
tetrahydrocannabinol (THC).

There is also provided a method for increasing plasma cannabidiolic acid (CBDA) concentration of a subject in need thereof, said method comprising administering an effective amount of:
at least one compound chosen from compound of formula (I), compound of formula (II), compound of formula (III) and compound of formula (IV); and
cannabidiolic acid (CBDA).

There is also provided a formulation comprising:
a shell; and
a fill material within the shell, the fill material comprising the composition as previously defined.

There is also provided a softgel formulation comprising:
a soft gelatin shell; and
a fill material within the shell, the fill material comprising the composition as previously defined.

There is also provided a softgel formulation comprising:
a soft gelatin shell; and
a fill material within the shell, the fill material comprising
a composition that comprises:
at least one compound chosen from compound of formula (I), compound of formula (II), compound of formula (III) and compound of formula (IV); and
a cannabinoid extract.

There is also provided a softgel formulation comprising:
a soft gelatin shell; and
a fill material within the shell, the fill material comprising
a composition that comprises:
at least one compound chosen from compound of formula (I), compound of formula (II), compound of formula (III) and compound of formula (IV); and
cannabidiolic acid (CBDA).

There is also provided a softgel formulation comprising:
a soft gelatin shell; and
a fill material within the shell, the fill material comprising
a composition that comprises:
at least one compound chosen from compound of formula (I), compound of formula (II), compound of formula (III) and compound of formula (IV); and
cannabidiol (CBD).

There is also provided a softgel formulation comprising:
a soft gelatin shell; and
a fill material within the shell, the fill material comprising
a composition that comprises:
at least one compound chosen from compound of formula (I), compound of formula (II), compound of formula (III) and compound of formula (IV); and
tetrahydrocannibinol (THC).

There is also provided a formulation, comprising:
a shell; and
a fill material within the shell, the fill material comprising:
about 100 mg to about 1400 mg of at least one compound chosen from compound of formula (I), compound of formula (II), compound of formula (III) and compound of formula (IV); and
about 0.1 mg to about 150 mg of at least one cannabinoid.

There is also provided a softgel formulation comprising:
a soft gelatin shell; and
a fill material within the shell, the fill material comprising:
about 100 mg to about 1400 mg of compound (IV); and
about 1 mg to about 100 mg of cannabidiolic acid (CBDA)

There is also provided a softgel formulation comprising:
a soft gelatin shell; and
a fill material within the shell, the fill material comprising:
about 100 mg to about 1400 mg of compound of formula (IV); and
about 1 mg to about 100 mg of cannabidiol (CBD).

There is also provided a softgel formulation comprising:
a soft gelatin shell; and
a fill material within the shell, the fill material comprising:
about 100 mg to about 1400 mg of compound of formula (IV); and
about 1 mg to about 10 mg of tetrahydrocannibinol (THC).

There is also provided a softgel formulation comprising:
a soft gelatin shell; and
a fill material within the shell, the fill material comprising:
about 25 mg to about 300 mg of a compound of formula (IV):
about 75 mg to about 1100 mg of EPA fish oil; and
about 5 mg to about 100 mg cannabidiolic acid (CBDA).

There is also provided a softgel formulation comprising:
a soft gelatin shell; and
a fill material within the shell, the fill material comprising:
about 25 mg to about 300 mg of a compound of formula (IV):
about 75 mg to about 1100 mg of EPA fish oil; and
about 5 mg to about 100 mg of cannabidiol (CBD).

There is also provided a softgel formulation comprising:
a soft gelatin shell; and
a fill material within the shell, the fill material comprising:
about 25 mg to about 300 mg of a compound of formula (IV):
about 75 mg to about 1100 mg of EPA fish oil; and
about 1 mg to about 10 mg of tetrahydrocannibinol (THC).

There is also provided a softgel formulation comprising:
a soft gelatin shell;
a fill material within the shell, the fill material comprising:
about 100 mg to about 1400 mg of compound of formula (IV);
about 75 mg to about 1100 mg of EPA fish oil; and
about 1 mg to about 100 mg of a cannabinoid extract.

There is also provided a softgel formulation comprising:
a soft gelatin shell; and
a fill material within the shell, the fill material comprising:
about 25 mg to about 300 mg of compound of formula (IV);
about 75 mg to about 1100 mg of EPA fish oil; and
about 100 mg to about 500 mg of a cannabinoid extract.

There is also provided a softgel formulation comprising:
a soft gelatin shell; and
a fill material within the shell, the fill material comprising:
about 25 mg to about 300 mg of compound of formula (IV);
about 75 mg to about 1100 mg of EPA fish oil; and
about 50 mg to about 300 mg of cannabidiolic acid (CBDA).

There is also provided a softgel formulation comprising:
a soft gelatin shell; and
a fill material within the shell, the fill material comprising:
about 25 mg to about 300 mg of compound of formula (IV);
about 75 mg to about 1100 mg of EPA fish oil; and
about 50 mg to about 300 mg of cannabidiol (CBD).

There is also provided a method of administering to a subject a dose between 1 mg/kg and 5 mg/kg dose of cannabidiolic acid (CBDA), said method comprising administering about 1 to about 10 softgels that comprises said CBDA.

There is also provided a method for increasing plasma cannabidiolic acid (CBDA) concentration of a subject in need thereof, said method comprising administering a dose of about 1 mg/kg to about 5 mg/kg dose of cannabidiolic acid (CBDA) by administering about 1 to 10 about softgels that comprise said CBDA.

There is also provided a method for increasing plasma cannabidiolic acid (CBDA) concentration of a subject in need thereof, said method comprising administering a dose of about 1 mg/kg/day to about 5 mg/kg/day of cannabidiolic acid (CBDA) by administering, per day, about 1 to 10 about softgels that comprise CBDA.

There is also provided a composition, comprising:
about 100 mg to about 1400 mg of at least one compound chosen from compound of formula (I), compound of formula (II), compound of formula (III) and compound of formula (IV); and
about 0.1 mg to about 150 mg of at least one cannabinoid.

There is also provided a composition comprising:
about 100 mg to about 1400 mg of compound (IV); and
about 1 mg to about 100 mg of cannabidiolic acid (CBDA)

There is also provided a composition comprising:
about 100 mg to about 1400 mg of compound of formula (IV); and
about 1 mg to about 100 mg of cannabidiol (CBD).

There is also provided a composition comprising:
about 100 mg to about 1400 mg of compound of formula (IV); and
about 1 mg to about 10 mg of tetrahydrocannibinol (THC).

There is also provided a composition comprising:
about 25 mg to about 300 mg of a compound of formula (IV):
about 75 mg to about 1100 mg of EPA fish oil; and
about 5 mg to about 100 mg cannabidiolic acid (CBDA).

There is also provided a composition comprising:
about 25 mg to about 300 mg of a compound of formula (IV):
about 75 mg to about 1100 mg of EPA fish oil; and
about 5 mg to about 100 mg of cannabidiol (CBD).

There is also provided a composition comprising:
about 25 mg to about 300 mg of a compound of formula (IV):
about 75 mg to about 1100 mg of EPA fish oil; and
about 1 mg to about 10 mg of tetrahydrocannibinol (THC).

There is also provided a composition comprising:
about 100 mg to about 1400 mg of compound of formula (IV);
about 75 mg to about 1100 mg of EPA fish oil; and
about 1 mg to about 100 mg of a cannabinoid extract.

There is also provided a composition comprising:
about 25 mg to about 300 mg of compound of formula (IV);
about 75 mg to about 1100 mg of EPA fish oil; and
about 100 mg to about 500 mg of a cannabinoid extract.

There is also provided a composition comprising:
about 25 mg to about 300 mg of compound of formula (IV);
about 75 mg to about 1100 mg of EPA fish oil; and
about 50 mg to about 300 mg of cannabidiolic acid (CBDA).

There is also provided a composition comprising:
about 25 mg to about 300 mg of compound of formula (IV);
about 75 mg to about 1100 mg of EPA fish oil; and
about 50 mg to about 300 mg of cannabidiol (CBD).

There is also provided a composition, comprising:
about 100 mg to about 1400 mg of at least one compound chosen from compound of formula (I), compound of formula (II), compound of formula (III) and compound of formula (IV); and
about 0.1 mg to about 150 mg of at least one cannabinoid.

There is also provided a composition comprising:
about 100 mg to about 1400 mg of at least one compound chosen from compound of formula (I), compound of formula (II), compound of formula (III) and compound of formula (IV); and
about 1 mg to about 100 mg of cannabidiolic acid (CBDA)

There is also provided a composition comprising:
about 100 mg to about 1400 mg of at least one compound chosen from compound of formula (I), compound of formula (II), compound of formula (III) and compound of formula (IV); and
about 1 mg to about 100 mg of cannabidiol (CBD).

There is also provided a composition comprising:
about 100 mg to about 1400 mg of at least one compound chosen from compound of formula (I), compound of formula (II), compound of formula (III) and compound of formula (IV); and
about 1 mg to about 10 mg of tetrahydrocannibinol (THC).

There is also provided a composition comprising:
about 25 mg to about 300 mg of at least one compound chosen from compound of formula (I), compound of formula (II), compound of formula (III) and compound of formula (IV):
about 75 mg to about 1100 mg of EPA fish oil; and
about 5 mg to about 100 mg cannabidiolic acid (CBDA).

There is also provided a composition comprising:
about 25 mg to about 300 mg of at least one compound chosen from compound of formula (I), compound of formula (II), compound of formula (III) and compound of formula (IV):
about 75 mg to about 1100 mg of EPA fish oil; and
about 5 mg to about 100 mg of cannabidiol (CBD).

There is also provided a composition comprising:
about 25 mg to about 300 mg of at least one compound chosen from compound of formula (I), compound of formula (II), compound of formula (III) and compound of formula (IV):
about 75 mg to about 1100 mg of EPA fish oil; and
about 1 mg to about 10 mg of tetrahydrocannibinol (THC).

There is also provided a composition comprising:
about 100 mg to about 1400 mg of at least one compound chosen from compound of formula (I), compound of formula (II), compound of formula (III) and compound of formula (IV);
about 75 mg to about 1100 mg of EPA fish oil; and
about 1 mg to about 100 mg of a cannabinoid extract.

There is also provided a composition comprising:
about 25 mg to about 300 mg of at least one compound chosen from compound of formula (I), compound of formula (II), compound of formula (III) and compound of formula (IV);
about 75 mg to about 1100 mg of EPA fish oil; and
about 100 mg to about 500 mg of a cannabinoid extract.

There is also provided a composition comprising:
about 25 mg to about 300 mg of at least one compound chosen from compound of formula (I), compound of formula (II), compound of formula (III) and compound of formula (IV);
about 75 mg to about 1100 mg of EPA fish oil; and
about 50 mg to about 300 mg of cannabidiolic acid (CBDA).

There is also provided a composition comprising:
about 25 mg to about 300 mg of at least one compound chosen from compound of formula (I), compound of formula (II), compound of formula (III) and compound of formula (IV);

about 75 mg to about 1100 mg of EPA fish oil; and
about 50 mg to about 300 mg of cannabidiol (CBD).

BRIEF DESCRIPTION OF THE FIGURES

Further features and advantages will become more readily apparent from the following description of specific embodiments as illustrated by way of examples in the appended figures wherein.

DETAILED DESCRIPTION OF THE DISCLOSURE

Figure 1:
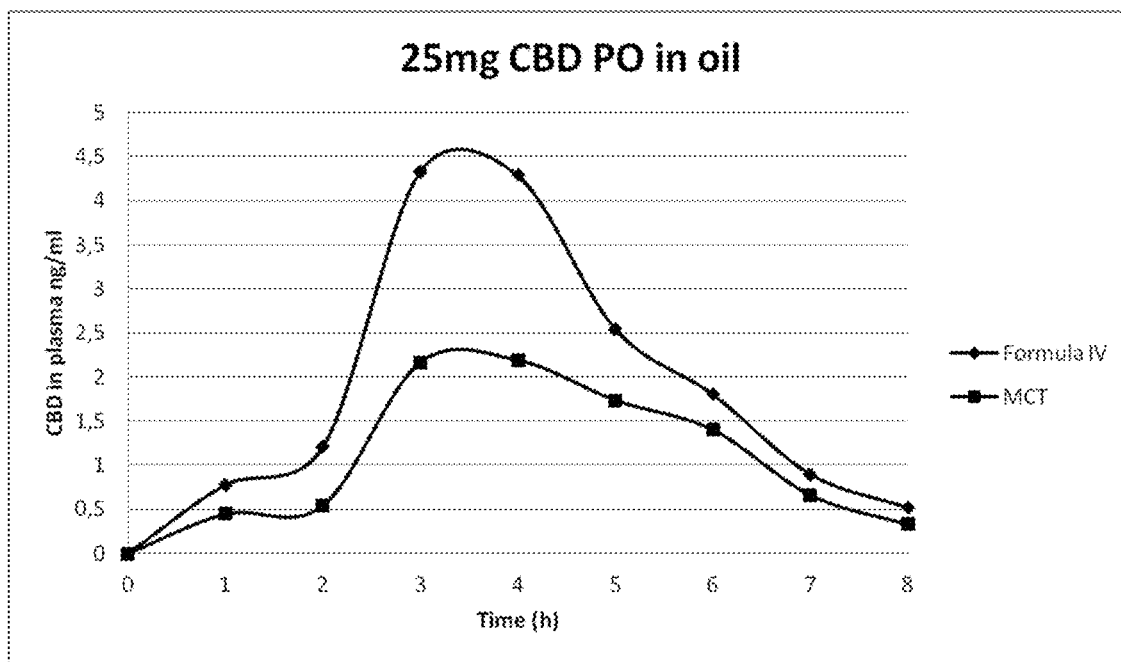
FIG. 1 represents a comparative human absorption crossover study of two different compositions of cannabidiol (CBD) which are medium chain triglyceride (MCT) and a composition comprising compound of formula (IV).

Further features and advantages of the previously-mentioned compounds will become more readily apparent from the following description of non-limiting examples.

The term "lipid" as used herein refers to as any fat-soluble (lipophilic), molecules, such as fats, fat-like substances, oils (such as animal oil, marine oil, krill oil, fish oil or vegetable oil), waxes, sterols (such as cholesterol, ergosterol, sitosterol, stigmasterol, fat-soluble vitamins (such as vitamins A, D, E and K), fatty acids, oxidized fatty acid (such as lipoxin, specialized pro-resolving mediators or epoxydes), fatty acids esters thereof, and various derivatives thereof such as monoglycerides, diglycerides, triglycerides, phospholipids, glycolipids, and cerebrosides and pharmaceutically acceptable salts thereof. For example, the lipid can be natural or synthetic.

The term "cannabinoid" as used herein refers to at least one compound chosen from THC (Tetrahydrocannabinol), THCA (Tetrahydrocannabinolic acid), CBD (Cannabidiol), CBDA (Cannabidiolic Acid), CBN (Cannabinol), CBG (Cannabigerol), CBC (Cannabichromene), CBL (Cannabicyclol), CBV (Cannabivarin), THCV (Tetrahydrocannabivarin), CBDV, (Cannabidivarin), CBCV (Cannabichromevarin), CBGV (Cannabigerovarin), CBGM, (Cannabigerol Monomethyl Ether), CBE (Cannabielsoin), CBT (Cannabicitran) and mixtures thereof.

The term "cannabinoid extract" as used herein refers to a cannabis or hemp concentrate that comprises at least one cannabinoid and that was produced with the use of a solvent to separate the desirable compounds of cannabis or hemp from the rest of the plant matter. The most common solvents used can include, for example, butane, propane, ethanol, and supercritical carbon dioxide ($CO_2$). Extracts can be in several forms like: full spectrum extract, broad spectrum extract or an isolate. Full spectrum extract is a cannabis concentrate produced that preserves the full cannabinoid and terpene contents of the raw cannabis or hemp plant. The goal of a full spectrum extract is to maintain the complex range of desirable compounds in a cannabis plant without altering them through decarboxylation or oxidation. Broad spectrum extract is a full spectrum extract without the tetrahydrocannabinol (THC). An isolate is a purified form of cannabinoids typically in the range of about 80 to about 99.9%.

The expression "effective amount" of a compound of the present disclosure is a quantity sufficient to, when administered to the subject, including a mammal, for example a human, effect beneficial or desired results, including clinical results, and, as such, an "effective amount" depends upon the context in which it is being applied. The amount of a given compound of the present disclosure that will correspond to such an amount will vary depending upon various factors, such as the given drug or compound, the pharmaceutical formulation, the route of administration, the identity of the subject or host being treated, and the like, but can nevertheless be routinely determined by one skilled in the art.

Terms of degree such as "about" and "approximately" as used herein mean a reasonable amount of deviation of the modified term such that the end result is not significantly changed. These terms of degree should be construed as including a deviation of at least ±10% of the modified term if this deviation would not negate the meaning of the word it modifies.

The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

For example, the subject in need thereof can be a bee, human, cat, dog, etc . . . .

For example, the at least one compound is said compound of formula (I).

For example, the at least one compound is said compound of formula (II).

For example, the at least one compound is said compound of formula (III).

For example, the at least one compound is said compound of formula (IV).

For example, the at least one compound is said compound of formula (I), said compound of formula (III) and said compound of formula (IV).

For example, the at least one compound is said compound of formula (I) and said compound of formula (IV).

For example, the at least one compound is said compound of formula (I) and said compound of formula (III).

For example, the at least one compound is said compound of formula (III) and said compound of formula (IV).

For example, the at least one compound can be for use in combination with at least one ingredient chosen from cannabis crude extract and hemp crude extract.

For example, the at least one ingredient and said at least one compound can be for simultaneous administration.

For example, the at least one ingredient and said at least one compound can be for separate administration.

For example, the at least one compound chosen from compound of formula (I), compound of formula (II), compound of formula (III) and compound of formula (IV) can be administered in combination with at least one ingredient chosen from cannabis crude extract and hemp crude extract.

For example, the at least one ingredient and said at least one compound can be administered simultaneously.

For example, the at least one ingredient and said at least one compound can be administered separately.

For example, said at least one compound is said compound of formula (IV).

For example, the at least one lipid comprises at least one omega-3 fatty acid.

For example, the at least one lipid comprises eicosapentaenoic acid (EPA).

For example, the at least one lipid comprises eicosapentaenoic acid (EPA) ethyl ester.

For example, the at least one lipid comprises eicosapentaenoic acid (EPA) triglyceride.

For example, the at least one lipid comprises krill oil.

For example, the at least one cannabinoid can be an isolated cannabinoid.

For example, the at least one lipid can be a synthetic lipid.

For example, the composition or formulation can further comprise a synthetic fish oil.

For example, the composition or formulation can further comprise a synthetic ester of fish oil.

For example, the composition or formulation can further comprise a synthetic ethyl ester of fish oil. For example, the composition or formulation can further comprise glycerol.

For example, the composition of formulation can comprise about 0.05% to about 30% by weight, based on the total weight of the composition, of the at least one cannabinoid.

For example, the composition of formulation can comprise about 0.1% to about 30% by weight, based on the total weight of the composition, of the at least one cannabinoid.

For example, the composition or formulation can comprise about 0.2% to about 30%, about 0.5% to about 25%, about 10% to about 25%, about 1.0% to about 20%, about 2.0% to about 20%, about 2.0% to about 30%, about 2.0% to about 20%, about 3.0% to about 20%, about 5.0% to about 20%, about 1.0% to about 15%, about 1.0% to about 10%, about 1.0% to about 10%, about 2.0% to about 10%, about 1.0% to about 15%, about 2.0% to about 12%, about 5.0% to about 15%, about 5.0% to about 10%, about 0.05% to about 2.0%, about 0.1% to about 10.0%, about 0.1% to about 5.0%, about 0.1% to about 2.0%, about 0.1% to about 1.0%, about 0.1% to about 0.8%, about 0.1% to about 0.6%, about 0.1% to about 0.4%, about 0.1% to about 0.3%, about 0.1% to about 0.2%, about 0.05% to about 50%, about 0.05% to about 75%, about 30% to about 60%, about 10% to about 90%, about 10% to about 85%, about 0.1% to about 75%, or about 0.05% to about 0.25%, by weight, based on the total weight of the composition or formulation, of the at least one cannabinoid.

For example, the composition or formulation can comprise about 0.2% to about 30%, about 0.5% to about 25%, about 10% to about 25%, about 1.0% to about 20%, about 2.0% to about 20%, about 2.0% to about 30%, about 2.0% to about 20%, about 3.0% to about 20%, about 5.0% to about 20%, about 1.0% to about 15%, about 1.0% to about 10%, about 1.0% to about 10%, about 2.0% to about 10%, about 1.0% to about 15%, about 2.0% to about 12%, about 5.0% to about 15%, about 5.0% to about 10%, about 0.05% to about 2.0%, about 0.1% to about 10.0%, about 0.1% to about 5.0%, about 0.1% to about 2.0%, about 0.1% to about 1.0%, about 0.1% to about 0.8%, about 0.1% to about 0.6%, about 0.1% to about 0.4%, about 0.1% to about 0.3%, about 0.1% to about 0.2%, about 0.05% to about 50%, about 0.05% to about 75%, about 30% to about 60%, about 10% to about 90%, about 10% to about 85%, about 0.1% to about 75%, or about 0.05% to about 0.25%, by weight, based on the total weight of the composition or formulation, of at least one compound chosen from compound of formula (I), compound of formula (II), compound of formula (III) and compound of formula (IV).

For example, the composition or formulation can comprise about 0.2% to about 30%, about 0.5% to about 25%, about 10% to about 25%, about 1.0% to about 20%, about 2.0% to about 20%, about 2.0% to about 30%, about 2.0% to about 20%, about 3.0% to about 20%, about 5.0% to about 20%, about 1.0% to about 15%, about 1.0% to about 10%, about 1.0% to about 10%, about 2.0% to about 10%, about 1.0% to about 15%, about 2.0% to about 12%, about 5.0% to about 15%, about 5.0% to about 10%, about 0.05% to about 2.0%, about 0.1% to about 10.0%, about 0.1% to about 5.0%, about 0.1% to about 2.0%, about 0.1% to about 1.0%, about 0.1% to about 0.8%, about 0.1% to about 0.6%, about 0.1% to about 0.4%, about 0.1% to about 0.3%, about 0.1% to about 0.2%, about 0.05% to about 50%, about 0.05% to about 75%, about 30% to about 60%, about 10% to about 90%, about 10% to about 85%, about 0.1% to about 75%, or about 0.05% to about 0.25%, by weight, based on the total weight of the composition or formulation, of at least one lipid.

For example, the composition or formulation can comprise about 0.2% to about 30%, about 0.5% to about 25%, about 10% to about 25%, about 1.0% to about 20%, about 2.0% to about 20%, about 2.0% to about 30%, about 2.0% to about 20%, about 3.0% to about 20%, about 5.0% to about 20%, about 1.0% to about 15%, about 1.0% to about 10%, about 1.0% to about 10%, about 2.0% to about 10%, about 1.0% to about 15%, about 2.0% to about 12%, about 5.0% to about 15%, about 5.0% to about 10%, about 0.05% to about 2.0%, about 0.1% to about 10.0%, about 0.1% to about 5.0%, about 0.1% to about 2.0%, about 0.1% to about 1.0%, about 0.1% to about 0.8%, about 0.1% to about 0.6%, about 0.1% to about 0.4%, about 0.1% to about 0.3%, about 0.1% to about 0.2%, about 0.05% to about 50%, about 0.05% to about 75%, about 30% to about 60%, about 10% to about 90%, about 10% to about 85%, about 0.1% to about 75%, or about 0.05% to about 0.25%, by weight, based on the total weight of the composition or formulation, of the at least one synthetic SN1 monoglyceride of a vegetal or animal oil.

For example, the composition or formulation can comprise about 0.2% to about 30%, about 0.5% to about 25%, about 10% to about 25%, about 1.0% to about 20%, about 2.0% to about 20%, about 2.0% to about 30%, about 2.0% to about 20%, about 3.0% to about 20%, about 5.0% to about 20%, about 1.0% to about 15%, about 1.0% to about 10%, about 1.0% to about 10%, about 2.0% to about 10%, about 1.0% to about 15%, about 2.0% to about 12%, about 5.0% to about 15%, about 5.0% to about 10%, about 0.05% to about 2.0%, about 0.1% to about 10.0%, about 0.1% to about 5.0%, about 0.1% to about 2.0%, about 0.1% to about 1.0%, about 0.1% to about 0.8%, about 0.1% to about 0.6%, about 0.1% to about 0.4%, about 0.1% to about 0.3%, about 0.1% to about 0.2%, about 0.05% to about 50%, about 0.05% to about 75%, about 30% to about 60%, about 10% to about 90%, about 10% to about 85%, about 0.1% to about 75%, or about 0.05% to about 0.25%, by weight, based on the total weight of the composition or formulation, of the at least one synthetic diglyceride of vegetal or animal oil selected from the group consisting of SN 1,2 synthetic diglyceride and SN 1,3 synthetic diglyceride.

For example, the composition or formulation can comprise about 1 mg to about 3000 mg, about 5 mg to about 2500 mg, about 10 mg to about 2000 mg, about 75 mg to about 1100 mg, about 25 mg to about 2000 mg, about 25 mg to about 300 mg, about 50 mg to about 1500 mg, about 100 mg to about 1400 mg, about 50 mg to about 300 mg, about 10 mg to about 500 mg, about 10 mg to about 100 mg, about 10 mg to about 250 mg, about 1 mg to about 100 mg, about 1 mg to about 10 mg, about 5 mg to about 50 mg, about 5 mg to about 100 mg, about 0.1 mg to about 150 mg, about 10 mg to about 250 mg or about 100 mg to about 500 mg, of at least one compound chosen from compound of formula (I), compound of formula (II), compound of formula (III) and compound of formula (IV).

For example, the composition or formulation can comprise about 1 mg to about 3000 mg, about 5 mg to about 2500 mg, about 10 mg to about 2000 mg, about 75 mg to about 1100 mg, about 25 mg to about 2000 mg, about 25 mg to about 300 mg, about 50 mg to about 1500 mg, about 100 mg to about 1400 mg, about 50 mg to about 300 mg, about 10 mg to about 500 mg, about 10 mg to about 100 mg, about 10 mg to about 250 mg, about 1 mg to about 100 mg, about 1 mg to about 10 mg, about 5 mg to about 50 mg, about 5 mg to about 100 mg, about 0.1 mg to about 150 mg, about 10 mg to about 250 mg or about 100 mg to about 500 mg, of at least one compound cannabinoid.

For example, the composition or formulation can comprise about 1 mg to about 3000 mg, about 5 mg to about 2500 mg, about 10 mg to about 2000 mg, about 75 mg to about 1100 mg, about 25 mg to about 2000 mg, about 25 mg to about 300 mg, about 50 mg to about 1500 mg, about 100 mg to about 1400 mg, about 50 mg to about 300 mg, about 10 mg to about 500 mg, about 10 mg to about 100 mg, about 10 mg to about 250 mg, about 1 mg to about 100 mg, about 1 mg to about 10 mg, about 5 mg to about 50 mg, about 5 mg to about 100 mg, about 0.1 mg to about 150 mg, about 10 mg to about 250 mg or about 100 mg to about 500 mg, of at least one lipid.

For example, the shell is a soft shell.
For example, the shell is a soft gelatin shell.
For example, the shell is a soft starch shell.
For example, the shell is a soft carrageenan shell.
For example, the shell is a hard shell.
For example, the shell is a hard gelatin shell.
For example, the shell is a hard hypromellose shell.
For example, the shell is a hard starch shell.
For example, the shell is a hard pullulan shell For example, as previously described, the composition or formulation can comprise the previously mentioned ingredients. For example, the composition or formulation can also consist essentially of such ingredients. For example, the composition or formulation can also consist of such ingredients.

Further features and advantages of the previously-mentioned compounds will become more readily apparent from the following description of non-limiting examples.

Example 1

54 mg of cannabidiol (CBD) was dissolved in 2.5 g of compound of formula (IV) to give a clear solution. 1.16 g of the mixture (25 mg CBD) was encapsulated in two (2) hard gel capsules (size 00) for absorption study. A pilot absorption study was conducted in one volunteer. The two (2) hard gel capsules were swallowed with a glass of water by the volunteer fasted for 10 h. 200 ul of blood was collected by a lancet in a heparinised microtube at T=0, 1, 2, 3, 4, 5, 6, 7 and 8 h. The plasma was analyzed by HPLC/MS/MS to quantify the CBD. A comparative study was conducted with the same amount of CBD but with MCT oil (medium-chain triglycerides oil) instead of compound of formula (IV). FIG. 1 shows the superiority of the compound of formula (IV) over the MCT oil on the absorption and bioavailability of CBD.

Example 2

Figure 2:
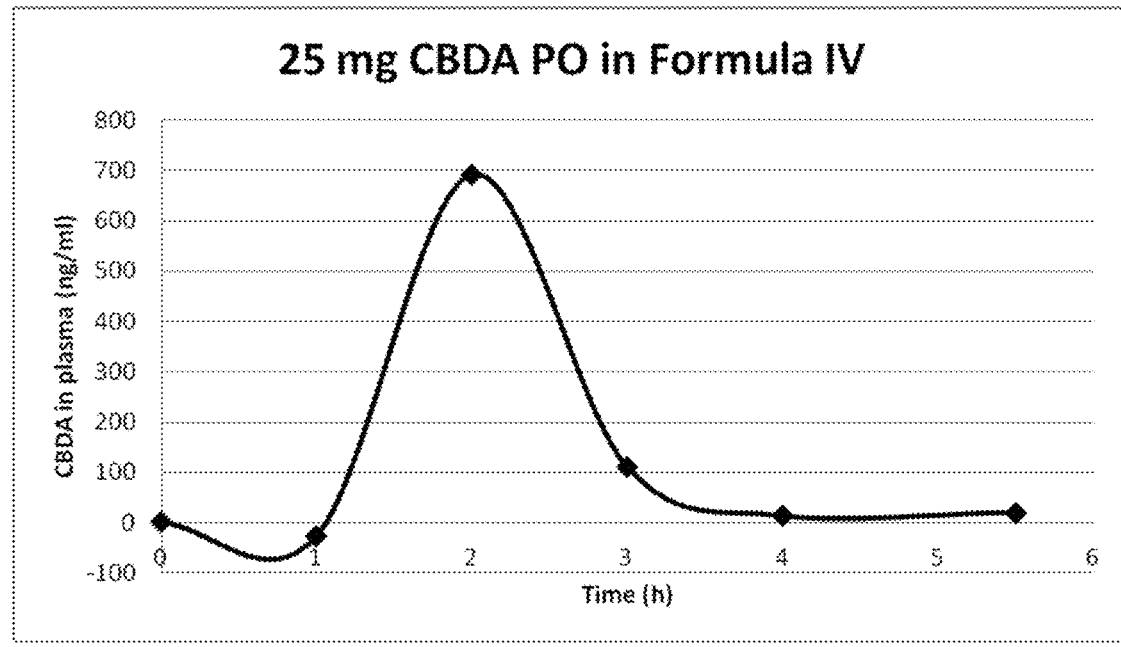
FIG. 2 represents a human absorption study of a composition of cannabidiolic acid (CBDA) in compound of formula (IV).

166 mg of cannabidiolic acid (CBDA) crude extract containing 20% CBDA was dissolved in 1.33 g of compound of formula (IV) to give a clear solution. 1.00 g of the mixture (25 mg CBDA) was encapsulated in two (2) hard gel capsules (size 00) for absorption study. A pilot absorption study was conducted in one volunteer. The two (2) hard gel capsules were swallowed with a glass of water by the volunteer fasted for 10 h. 200 ul of blood was collected by a lancet in a heparinised microtube at T=0, 1, 2, 3, 4, 5, 6, 7 and 8 h. The plasma was analyzed by HPLC/MS/MS to quantify the CBDA. FIG. 2 shows the absorption and bioavailability profile of CBDA in plasma.

Example 3

Figure 3:
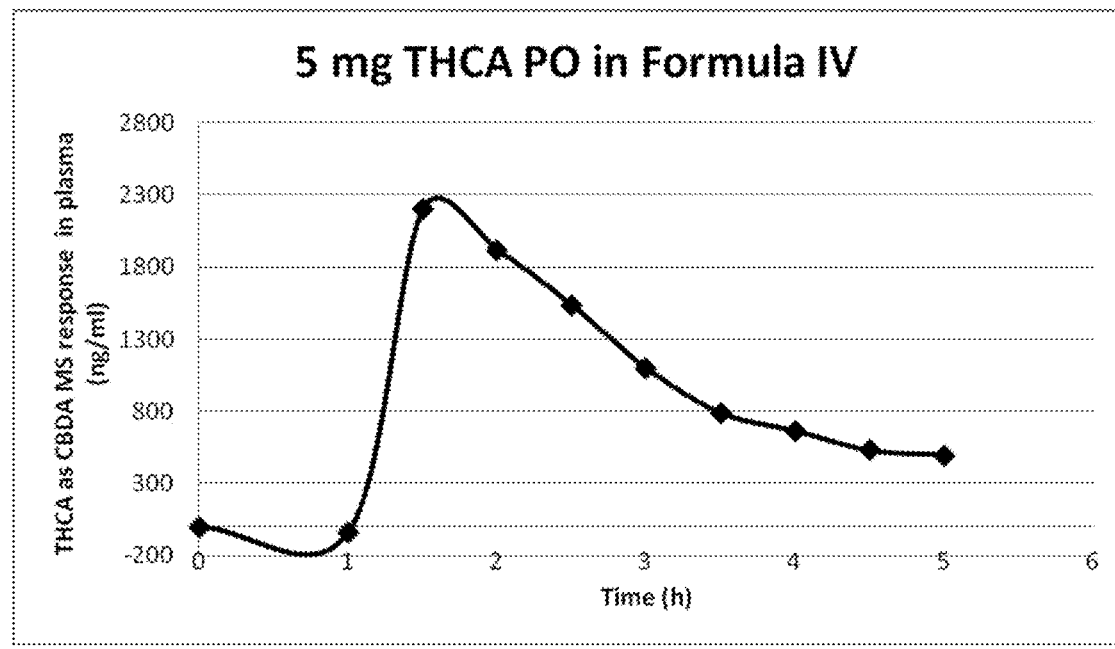
FIG. 3 represents a human absorption study of a composition of tetrahydrocannabinol (THC) in compound of formula (IV).

106 mg of tetrahydrocannabinolic acid (THCA) crude extract containing 20% THCA was dissolved in 4.00 g of compound of formula (IV) to give a clear solution. 1.00 g of the mixture (5 mg THCA) was encapsulated in two (2) hard gel capsules (size 00) for absorption study. A pilot absorption study was conducted in one volunteer. The two (2) hard gel capsules were swallowed with a glass of water by the volunteer fasted for 10 h. 200 ul of blood was collected by a lancet in a heparinised microtube at T=0, 1, 2, 3, 4, 5, 6, 7 and 8 h. The plasma was analyzed by HPLC/MS/MS to quantify the THCA (the calibration curve was made with CBDA). FIG. 3 shows the absorption and bioavailability profile of THCA in plasma.

Example 4

Preparation of a Composition (Composition 1) Comprising Compound IV and CBDA.

Cannabis dried flowers (7 g) was extracted with ethanol (100 ml) for 72 h at room temperature. The flowers was filtered and the ethanol was removed under vacuum without heating to give the cannabinoid crude extract (1.9 g) containing 85% CBDA and 4% THCA. The crude extract (315 mg) was dissolved in a mixture of compound of formula (IV) and EPA concentrated ethyl ester fish oil (3.5 g) to give composition 1.

Example 5

Human Absorption Study of Composition 1 Comprising Compound IV and a Cannabinoid Crude Extract Containing 85% CBDA.

Figure 4:
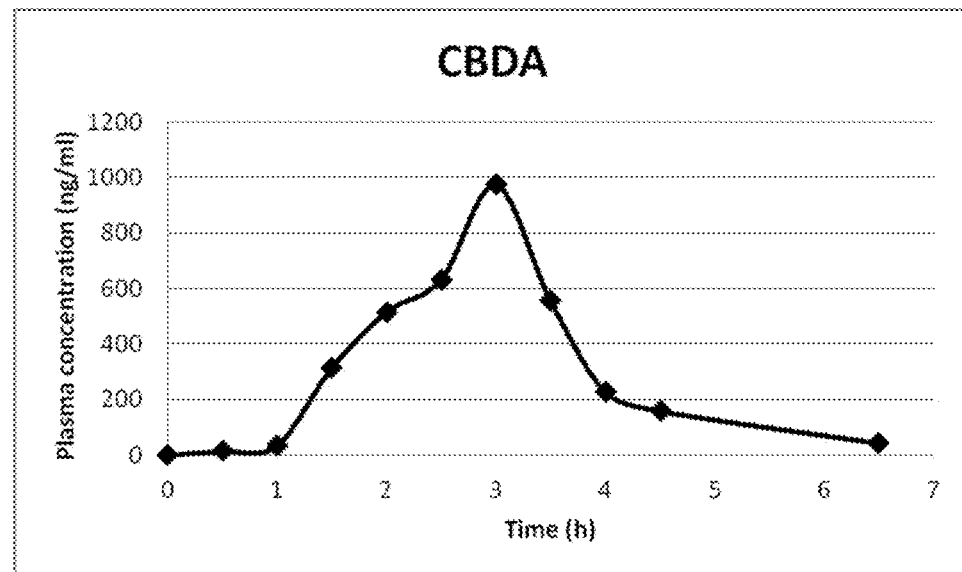
FIG. 4 represents a human absorption study of a composition containing a cannabinoids extract from cannabis in of compound of formula (IV) and EPA fish oil.
Figure 5:
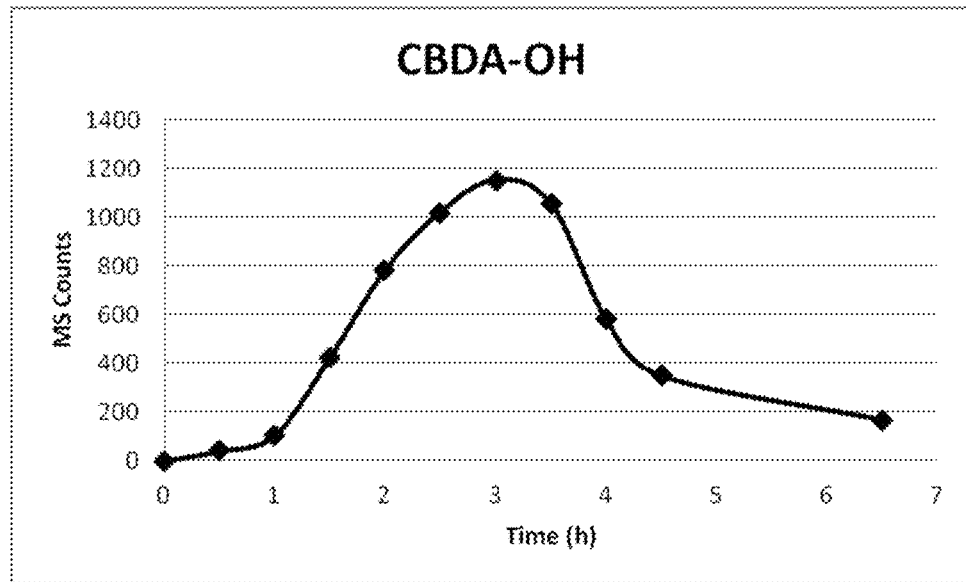
FIG. 5 represents the hydroxyl metabolite of CBDA in plasma following oral administration of a composition containing a cannabinoids extract from cannabis in of compound of formula (IV) and EPA fish oil.
Figure 6:
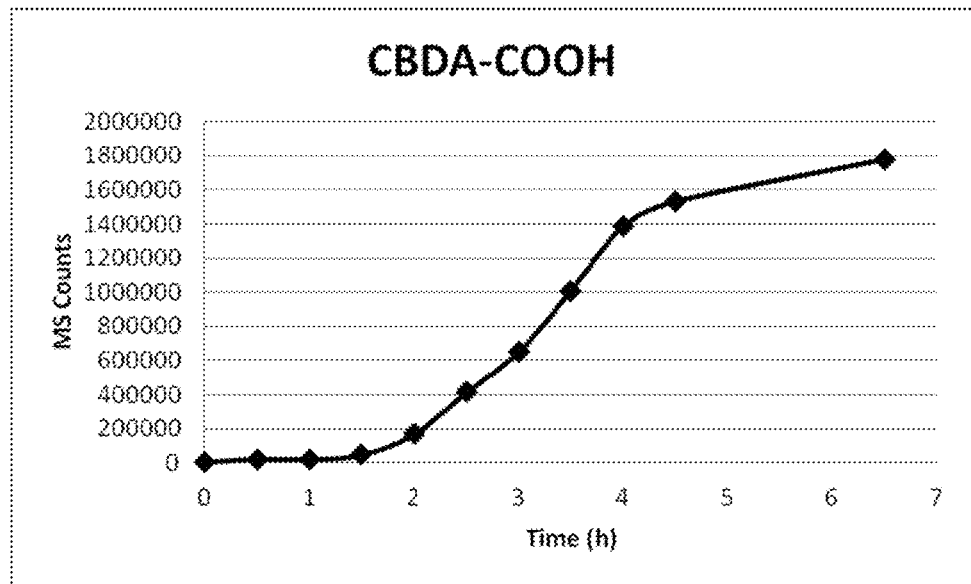
FIG. 6 represents the carboxylic acid metabolite of CBDA in plasma following oral administration of a composition containing a cannabinoids extract from cannabis in of compound of formula (IV) and EPA fish oil.

2.47 g of composition 1 was encapsulated in four (4) hard gel capsules (size 00) for absorption study. A pilot absorption study was conducted in one volunteer. The four (4) hard gel capsules were swallowed with a glass of water by the volunteer fasted for 10 h. 200 ul of blood was collected by a lancet in a heparinised microtube at T=0, 0.5, 1, 1.5, 2, 2.5, 3, 3.5, 4, 4.5, and 6.5 h. The plasma was analyzed by HPLC/MS/MS to quantify the CBDA. FIG. 4 shows the absorption and bioavailability profile of CBDA in plasma. FIG. 5 shows the hydroxy metabolite of CBDA in plasma and FIG. 6 the carboxylic acid metabolite of CBDA in plasma.

Most of the cannabinoids lipid formulations currently on the market are with medium chain triglycerides (MCT) or seed oil. Most of the seed oil are rich in omega-6 fatty acid who are pro-inflammatory hence the need for an omega-3 rich carrier oil who can resolve inflammation. Compounds of formula I, III and IV are monoglycerides of omega-3 fatty acid and proved to have an inflammation resolution activity (Morin, C., et al., *Eicosapentaenoic acid monoglyceride resolves inflammation in an ex vivo model of human peripheral blood mononuclear cell*. European Journal of Pharmacology, 2017. 807: p. 205-211). In addition, the SN1 monoglyceride form is an isoform of the 2-arachidonoylglycerol (2-AG) a well-known endocannabinoids (Sugiura, T., et al., *Evidence That the Cannabinoid CB1 Receptor Is a 2-Arachidonoylglycerol Receptor: STRUCTURE-ACTIVITY RELATIONSHIP OF 2-ARACHIDONOYLGLYCEROL, ETHER-LINKED ANALOGUES, AND RELATED COMPOUNDS*. Journal of Biological Chemistry, 1999. 274(5): p. 2794-2801) and this close structural relationship made the compounds of formula I to IV a perfect synergistic choice for cannabinoids formulation.

Another aspect of the present disclosure is the high solubility of cannabinoids or cannabis and hemp crude extract in compound of formula IV. One of the only cannabinoid oral formulations on the market is EPIDIOLEX®, a cannabidiol (CBD) in corn oil at 100 mg/ml. The CBD solubility in corn oil is approx. 300 mg/ml and in a formulation containing compound of formula IV and EPA fish oil, the solubility is 400 mg/ml. This 33% increase of solubility with the ability of the formulation containing compound of formula IV and EPA fish oil to form an emulsion spontaneously in contact of water or stomach fluid or intestinal fluid, make possible an oral self emulsifying cannabinoids delivery system. In addition, this high solubility also opens the door to a high potency softgel especially for the non-psychotic cannabinoids like cannabidiol (CBD) and cannabidiolic acid (CBDA). A high potency cannabidiolic acid (CBDA) in compound of formula III can be a natural replacement of conventional NSAID drug by the COX-2 inhibition property of CBDA and pro-resolution action of compound of formula IV. In the case of cannabis or hemp flowers extract coming in from the cold extraction (without any heating) the CBD and THC will remain in their CBDA and THCA native form. In this form, CBDA is a known COX-2 inhibitor (Takeda, S., et al., *Cannabidiolic Acid as a Selective Cyclooxygenase-2 Inhibitory Component in Cannabis*. Drug Metabolism and Disposition, 2008. 36(9): p. 1917-1921) and THCA have no psychotropic effect who makes the cold crude extract the perfect match with the compound of formula IV.

The oral bioavailability of cannabinoids are quite low, Health Canada states an oral bioavailability of THC of only 10%. We found that when formulated in compound of formula IV, CBD is 200% more bioavailable that MCT oil at a low dose of 25 mg. To be effective as COX-2 inhibitors, the CBD or cannabinoid extract containing CBDA oral doses must be around 5 mg/kg (Gallily, R., Yekhtin, Z. and Hanuš, L. (2015) *Overcoming the Bell-Shaped Dose-Response of Cannabidiol by Using Cannabis Extract Enriched in Cannabidiol*. Pharmacology & Pharmacy, 6, 75-85). At this high dose, orally administered CBD (400 mg in corn oil) give a Cmax of only 181 ng/ml in plasma (Manini, A. F., et al., *Safety and pharmacokinetics of oral cannabidiol when administered concomitantly with intravenous fentanyl in humans*. Journal of addiction medicine, 2015. 9(3): p. 204-210). With our formulation of a cannabinoid extract containing 170 mg of CBDA in compound of formula IV give a Cmax of 1000 ng/ml in plasma (500% increase of the Cmax for half of the dose). At our knowledge, it's the first time that a Cmax of a cannabinoids of 1000 ng/ml was reported in the scientific literature.

While the compounds, compositions, methods and uses thereof have been described in connection with specific embodiments thereof, it will be understood that they can be further modified and this application is intended to cover any variations, uses, or adaptations of the compounds, compositions, methods and uses thereof following, in general, the principles described in the present document and including such departures from the present disclosure as come within known or customary practice within the art to which the present document pertains and as may be applied to the features hereinbefore set forth, and as follows in the scope of the appended claims.

What is claimed is:

1. A composition consisting essentially of:
   a synthetic SN1 monoglyceride selected from the group consisting of a compound of formula (I), a compound of formula (II), a compound of formula (III), a compound of formula (IV) and mixtures thereof:

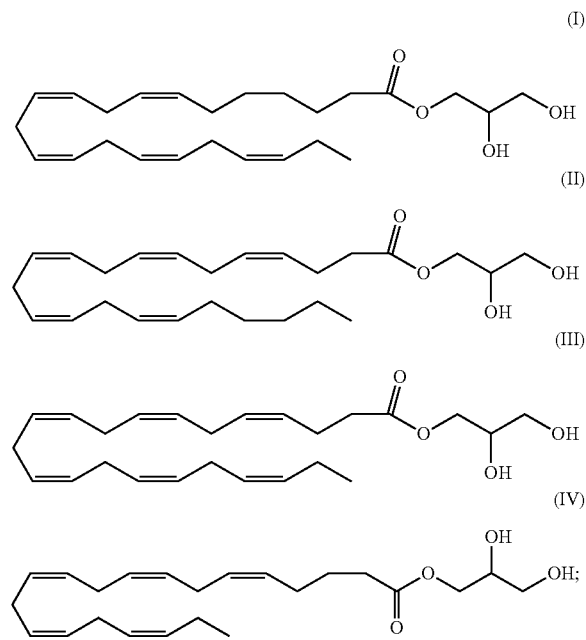 [SMILES: CC/C=C\C/C=C\C/C=C\C/C=C\C/C=C\CCCCCC(=O)OCC(O)CO ; CCCCC/C=C\C/C=C\C/C=C\C/C=C\C/C=C\CCC(=O)OCC(O)CO ; CC/C=C\C/C=C\C/C=C\C/C=C\C/C=C\C/C=C\CCC(=O)OCC(O)CO ; CC/C=C\C/C=C\C/C=C\C/C=C\C/C=C\CCCC(=O)OCC(O)CO]

a SN 1,2 synthetic diglyceride;
   a SN 1,3 synthetic diglyceride; and
   an isolated cannabinoid selected from the group consisting of an isolated Cannabidiol (CBD), an isolated Cannabidiolic Acid (CBDA), an isolated Tetrahydrocannabinol (THC) and mixtures thereof.

2. The composition of claim 1, wherein the synthetic SN1 monoglyceride is the compound of formula (I).

3. The composition of claim 1, wherein the synthetic SN1 monoglyceride is the compound of formula (II).

4. The composition of claim 1, wherein the synthetic SN1 monoglyceride is the compound of formula (III).

5. The composition of claim 1, wherein the synthetic SN1 monoglyceride is the compound of formula (IV).

6. The composition of claim 1, wherein the isolated cannabinoid is isolated Cannabidiol (CBD).

7. The composition of claim 1, wherein the isolated cannabinoid is isolated Cannabidiolic Acid (CBDA).

8. The composition of claim 1, wherein the isolated cannabinoid is isolated Tetrahydrocannabinol (THC).

9. The composition of claim 1, wherein the synthetic SN1 monoglyceride is the compound of formula (I), and wherein the isolated cannabinoid is isolated Cannabidiol (CBD).

10. The composition of claim 1, wherein the synthetic SN1 monoglyceride is the compound of formula (II), and wherein the isolated cannabinoid is isolated Cannabidiol (CBD).

11. The composition of claim 1, wherein the synthetic SN1 monoglyceride is the compound of formula (III), and wherein the isolated cannabinoid is isolated Cannabidiol (CBD).

12. The composition of claim 1, wherein the synthetic SN1 monoglyceride is the compound of formula (IV), and wherein the isolated cannabinoid is isolated Cannabidiol (CBD).

* * * * *